(12) United States Patent
Gagesch et al.

(10) Patent No.: US 8,374,416 B2
(45) Date of Patent: Feb. 12, 2013

(54) DEVICE AND METHOD FOR LOCALIZATION OF A TISSUE VARIATION FOR A BIOPSY

(75) Inventors: Gerlinde Marlene Gagesch, Unterschleβheim (DE); Christina Singer, Kirchchrenbach (DE)

(73) Assignee: Siemens Aktiengesellschaft, Munich (DE)

( * ) Notice: Subject to any disclaimer, the term of this patent is extended or adjusted under 35 U.S.C. 154(b) by 573 days.

(21) Appl. No.: 12/575,606

(22) Filed: Oct. 8, 2009

(65) Prior Publication Data

US 2010/0092062 A1 Apr. 15, 2010

(30) Foreign Application Priority Data

Oct. 8, 2008 (DE) .......................... 10 2008 050 844

(51) Int. Cl.
 *G06K 9/00* (2006.01)
 *A61B 6/02* (2006.01)
(52) U.S. Cl. ........................... 382/132; 382/131; 378/41

(58) Field of Classification Search .................. 382/131, 382/132; 378/37, 41
See application file for complete search history.

(56) References Cited

U.S. PATENT DOCUMENTS

| 4,544,949 | A | * | 10/1985 | Kurihara ..................... 378/98.12 |
| 4,888,794 | A | | 12/1989 | Haaker et al. |
| 5,583,345 | A | * | 12/1996 | Kohgami et al. ............. 250/580 |
| 6,081,582 | A | * | 6/2000 | Mazess et al. ................ 378/146 |
| 8,194,953 | B2 | * | 6/2012 | Xie et al. ...................... 382/128 |
| 2005/0207529 | A1 | * | 9/2005 | Boese et al. .................... 378/41 |

FOREIGN PATENT DOCUMENTS

DE 634 152 3/1950

* cited by examiner

*Primary Examiner* — Alexander H Taningco
(74) *Attorney, Agent, or Firm* — Schiff Hardin LLP

(57) ABSTRACT

In a device and associated method for localization of a tissue variation for a biopsy, a first tissue variation within a first image of a stereo exposure is marked after limitation of a biopsy-capable region within an overview image. The search region for this localized first tissue variation in the second image of the stereo exposure is predetermined by a search corridor in the second image.

8 Claims, 4 Drawing Sheets

DEVICE AND METHOD FOR LOCALIZATION OF A TISSUE VARIATION FOR A BIOPSY

BACKGROUND OF THE INVENTION

1. Field of the Invention

The present invention concerns a device and method for localization of a tissue variation for a biopsy, and in particular to such a device and method employing x-ray imaging.

2. Description of the Prior Art

The benign or malignant nature of a tissue variation can be determined by means of a tissue sample extraction and subsequent histological examinations. The determination of localizations of tissue variations is based on x-ray images. In order to localize tissue variations, for example in the breast, an overview x-ray exposure of the breast is acquired first. A tissue variation can be localized using the generated overview x-ray exposure. In the continuation of the examination, two additional x-ray exposures are made with different alignments of the x-ray focus relative to the breast. These x-ray exposures are also designated as stereo image exposures. Starting from a vertical alignment of a central ray emanating from an x-ray head, a first x-ray image and a second x-ray image of the breast are produced from different acquisition angles relative to said breast.

It is the goal of a treating physician to determine local sites that belong together in the first x-ray image and in the second x-ray image, which local sites could be used for as a target site for a biopsy (meaning for the extraction of a tissue sample). Since a number of tissue variations can be visible in the x-ray images, however, it is very difficult to determine local sites in the x-ray images that can be biopsied. Additionally, the physician must already decide using the overview image whether a visible abnormality (for example at the border of the x-ray exposure) can be biopsied in the continuation of the examination. In the conventional procedure it may occur that, due to the assessment of a tissue variation that can be biopsied that is situated in the border of the overview image, the breast must be repositioned on the x-ray placement table and a new overview x-ray image produced, even though this local site would have been reachable in a biopsy. It may also occur that a tissue variation at the border region is classified as being able to be biopsied and additional x-ray images have been produced, but no further conclusion in relation to a biopsy capability with regard a specific locality could be derived from these additional images. Such a procedure entails the disadvantages that the duration of the examination is extended by the repositioning and the additional x-ray acquisitions cause the radiation exposure for the patient to be increased.

SUMMARY OF THE INVENTION

An object of the present invention is to provide an arrangement and an associated method for localization of tissue variations for a biopsy wherein the above disadvantages are avoided or alleviated.

The above object is achieved in accordance with the present invention in a method and device for localization of a tissue variation in an examination subject for a biopsy, wherein a first tissue variation within a first image of a stereo exposure of the subject is marked, after limitation of a biopsy-capable region within an overview image. The search region for this localized first tissue variation in the second image of the stereo exposure is predetermined by a search corridor in the second image.

The invention has the advantage that a conclusion about a volume that can be biopsied can be made using the overview image. The subject matter of the invention additionally offers the user a certain and fast detection of a localization that can be biopsied.

The invention also has the advantage that a determination of the coordinates for a biopsy of a tissue variation can already be classified in advance as ascertainable. This brings with it the additional advantage that the number of x-ray exposures is reduced to a minimum, and therefore an additional radiation exposure for the patient is avoided.

DESCRIPTION OF THE PREFERRED EMBODIMENTS

According to the invention, through a visualization of a volume of a subject that can be biopsied in an image, the viewer is able to decide—using an objective and reliable demarcation—whether a tissue variation (for example a calcification) can be reached for a tissue extraction. Unnecessary repositioning, overview images and stereo x-ray images are thus avoided.

The examination workflow (for example of a breast biopsy) is simplified and accelerated in that the subject matter of the invention assists the physician in the establishment of a localization to be biopsied. For this purpose, in addition to a general conclusion of whether a biopsy at selected points can be implemented with the current positioning of the breast, a significant search region for corresponding tissue variations in the stereo image exposure is provided to the physician for a certain and fast examination workflow. The physician can then associate identical tissue variations with one another in a limited range for a subsequent biopsy. The coordinates for the tissue variation can then be determined from the positions of the identical tissue variations in the first and second x-ray images.

Figure 3:
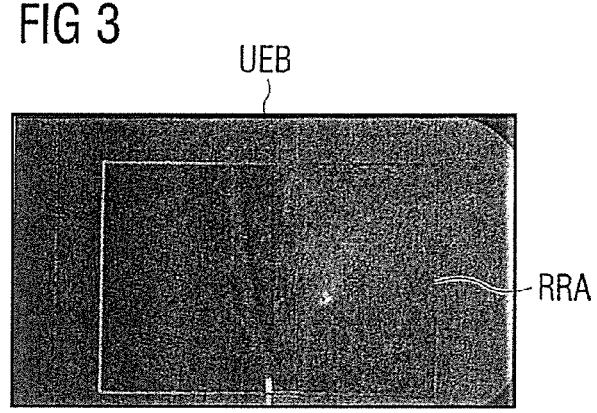
FIG. 3 is a visualization of the volume that can be biopsied in the device and method according to the invention.

For the following description, the volume of a breast that can be biopsied has the shape of a cuboid that is known in terms of its dimensions. Its height is predetermined by the compression thickness. In order to display the achievable volume in the overview image, the lower surface of the cuboid is projected onto the detector plane and converted into pixel coordinates in a first processing step. Starting from the detector plane, a back-projection of the beam path to the beam source ensues. The rectangular radiation field at the level of the compressed top side of the breast is then visualized in the overview image in the form of a rectangular frame as shown in FIG. 3. With this limitation it is ensured that, if a point is arranged within the projected rectangle, this then also lies within the biopsy volume that can be reached.

To indicate the search corridor, in a second image of a stereo image exposure, a first tissue variation is marked as a starting point. Using the geometric factors of the cuboid and taking into account the marked tissue variation, a region in the respective other image of the stereo image exposure can be determined in which the point corresponding to the first tissue variation is located. According to FIG. 4, the coordinates of the first tissue variation are determined in the first image. Via an individual consideration of a partial x-ray beam, the penetration points DP1, DP2 on the cuboid are determined. These penetration points DP1, DP2 are projected into the second image of the stereo image exposure and connected with one another. The corresponding point at the stereo image marked in the first image is located on this connection line. For the physician this entails the advantage of a fast location of a corresponding point MA1" in the second image relative to the respective point MA1 in the first image.

Figure 1:
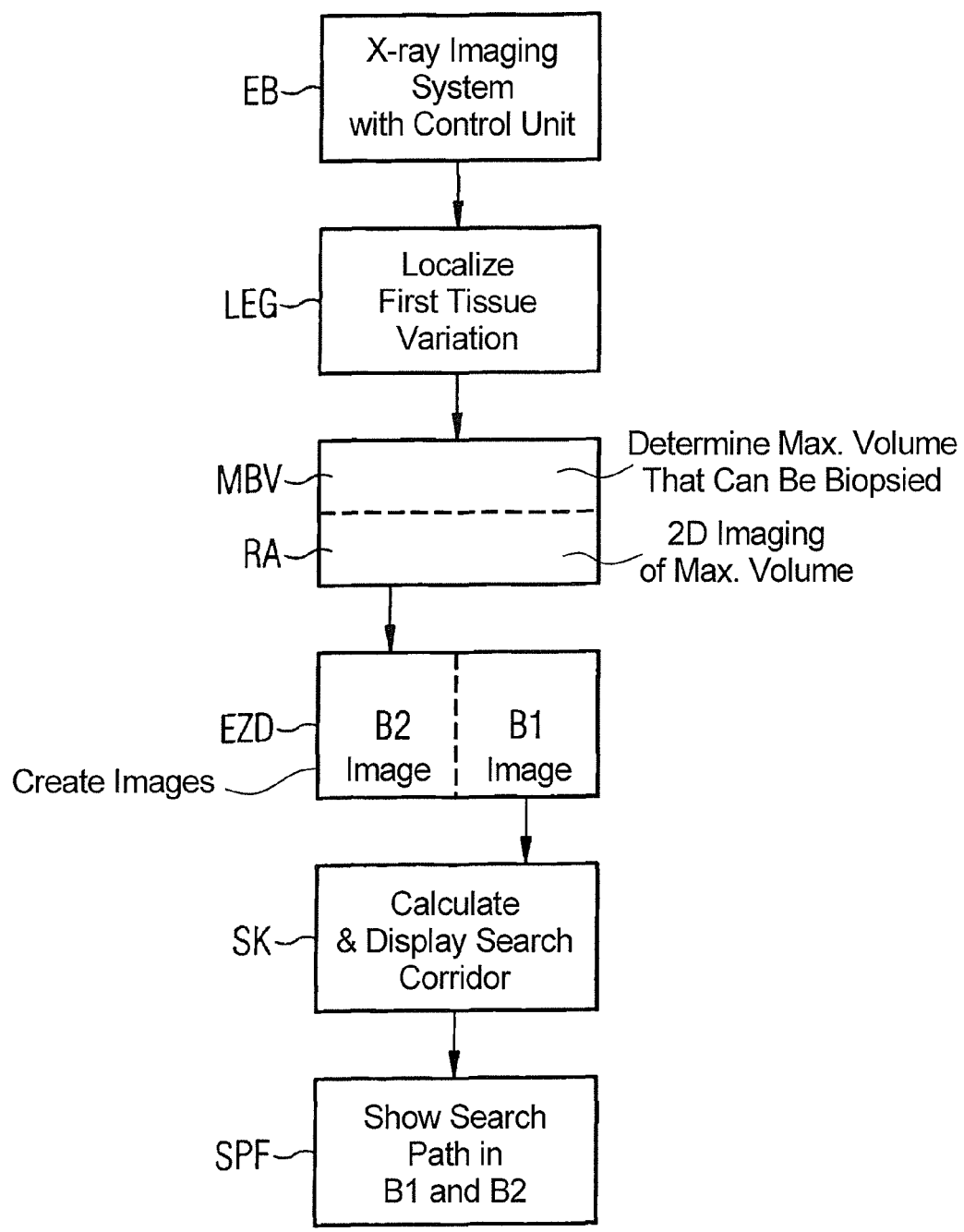
FIG. 1 is a block diagram showing the basic components of an embodiment of a device according to the invention.

A block diagram for the determination of a biopsy capability of a tissue variation is shown in FIG. 1. The device modules EB, EZD, MBV, RA, SK, LEG, SPF to determine a biopsy capability of a tissue variation are shown in the block diagram. The first module EB is an x-ray imaging system operable by a control unit that serves to obtain an overview image UEB; the fifth module LEG serves to localize a first tissue variation; the third module MBV serves to determine a maximum volume that can be biopsied on the basis of the overview image; the sub-module RA serves for the 2D imaging of the volume that can be biopsied in the overview image; the second module EZD serves to create a first and second image B1, B2; the fourth module SK serves to calculate and display a search corridor K for the localization of a first tissue variation localized in the second image B2; and the search path is visualized in the first and second image in the sixth module SPF.

After a positioning of the patient and a fixing of the breast, starting from the first module EB an overview image UEB is created. The overview exposure UEB can be an x-ray exposure of the subject, for example.

In the fifth module LEG, the overview image UEB is searched by means of an image recognition program for tissue variations, in particular for calcifications, and the tissue variations are respectively marked MA1, ..., MAn. A visual inspection and marking of the detected tissue variations in the overview image exposure UEB can likewise be conducted by the physician.

As described in the following, the volume MB that can be biopsied is determined by the third module MBV based on the height c of the subject M, the distance I of the placement surface AF from the x-ray source RQ and the distance of the placement surface AF from the detector surface DF. Initialized by the sub-module RA in the third module MBV, a volume that can be biopsied is overlaid into the overview image UEB in a 2D view by means of a rectangular frame RRA. This limitation is visualized within the overview image UEB, for example as a rectangular frame as shown in FIG. 3.

An x-ray exposure consisting of a first image and a second image B1, B2 is produced from the subject M by the second module EZD.

Starting from a first tissue variation localized in the first image B1, a search corridor K in the second image B2 is determined by the fourth module SK. The determination of this search corridor is described in detail below.

In the sixth module SPF, the determined search path is applied to associate the first tissue variation from the first image with the same first tissue variation in the second image B2. In a simple case this search path can be a straight line K that is overlaid in the second image B2 starting from the first tissue variation in the first image B1. The processing in the individual modules and the visualization respectively ensue controlled by a processor.

Figure 2:
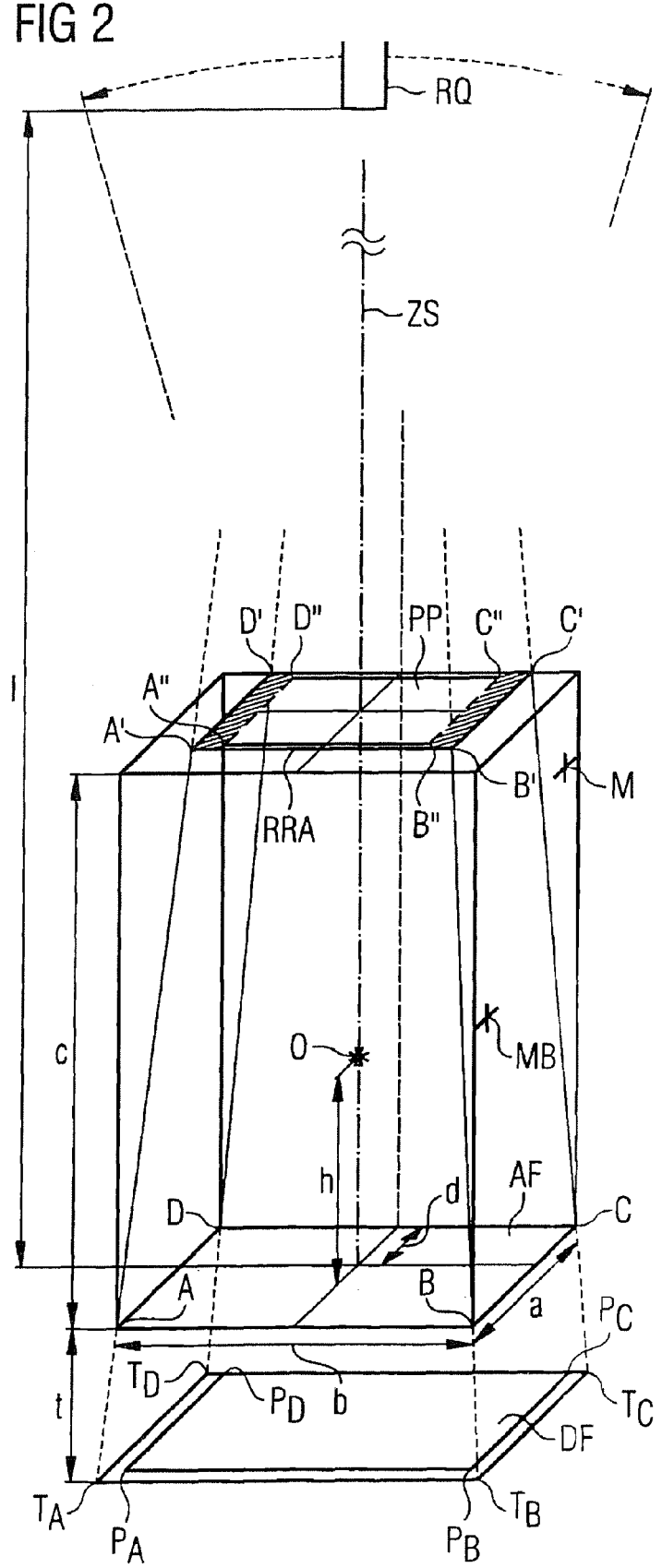
FIG. 2 schematically illustrates the operation of the device and method according to the invention.

In FIG. 2, the limitation of the volume of the breast that can be biopsied is explained using a schematic drawing. In this overview image, the breast is schematically shown as an element M; the placement surface on the subject table is designated with AF; the used detector surface is designated as DF and a radiation source that can be fashioned as an x-ray source is designated as RQ. The limitation of a possible volume that can be biopsied is designated with MB, and its two-dimensional visualization is designated by means of the frame RRA. It is to be taken into account that the volume MB that can be biopsied decreases depending on the deflection of the x-ray source corresponding to the deflection of the x-ray source RQ, while maintaining the support surface AF in the upper third. The border regions are separately marked in FIG. 2. The region PP that can be biopsied is thus reduced by the rectangular areas A', A", D', D" and B', B", C', C". The frame length of the frame RRA is determined by the corners of the placement surface AF across the projection of said placement surface and its conversion at the detector surface DF.

The corners of the placement surface AF result from $$A = \left(a - d, -\frac{b}{2}, 0\right), B = \left(a - d, -\frac{b}{2}\right)$$

$$C = \left(-d, \frac{b}{2}\right), D = \left(-d, -\frac{b}{2}\right).$$

The position of the x-ray source is known via $X = (I)$. The orthogonal projection of the placement surface AF on the detector surface DF results from $z = -t$ and $Y = (-t)$. The projection of the corners A, B, C and D of the placement surface on the detector plane DF results from $$P_A = \begin{pmatrix} a - d \cdot \frac{1+t}{1} \\ -\frac{b}{2} \cdot \frac{1+t}{1} \\ -t \end{pmatrix}$$

$$P_B = \begin{pmatrix} a - d \cdot \frac{1+t}{1} \\ \frac{b}{2} \cdot \frac{1+t}{1} \\ -t \end{pmatrix}$$

$$P_C = \begin{pmatrix} -d \cdot \frac{1+t}{1} \\ \frac{b}{2} \cdot \frac{1+t}{1} \\ -t \end{pmatrix}$$

$$P_D = \begin{pmatrix} -d \cdot \frac{1+t}{1} \\ -\frac{b}{2} \cdot \frac{1+t}{1} \\ -t \end{pmatrix}$$

These points are translated into the coordinate system of the detector image. The detector surface has n pixels in the x-direction and m pixels in the y-direction. The point $(\eta\zeta)$ describes a point in the image plane.

The corners TA, TB, TC and TD of a possible detector surface are thus expressed in pixel coordinates:

$$T_A = \frac{1+t}{p \cdot 1}\begin{pmatrix} \frac{b}{2} \\ d-a \end{pmatrix} + \begin{pmatrix} \eta \\ \zeta - \frac{d}{p} \end{pmatrix}$$

$$T_B = \frac{1+t}{p \cdot 1}\begin{pmatrix} -\frac{b}{2} \\ d-a \end{pmatrix} + \begin{pmatrix} \eta \\ \zeta - \frac{d}{p} \end{pmatrix}$$

$$T_C = \frac{1+t}{p \cdot 1}\begin{pmatrix} -\frac{b}{2} \\ d \end{pmatrix} + \begin{pmatrix} \eta \\ \zeta - \frac{d}{p} \end{pmatrix}$$

$$T_D = \frac{1+t}{p \cdot 1}\begin{pmatrix} \frac{b}{2} \\ d \end{pmatrix} + \begin{pmatrix} \eta \\ \zeta - \frac{d}{p} \end{pmatrix}$$

A truncated pyramid having a base at the detector surface DF can be determined as a volume that can be biopsied. For example, the volume that can be biopsied is visualized as a rectangle in the 2D overview image. It is possible to show the volume that can be biopsied in a 3D representation at a visualization unit.

The rectangular limitation RA with the corners A', B', C' and D' is overlaid in the overview exposure UEB in FIG. 3. The physician is thus already shown in an early examination stage whether the imaged section of the breast can remain in the current position. Given a tissue variation situated outside of the marking RRA, the localization with the tissue variation must be positioned closer to the central beam of the x-ray source. After this correction, the examination workflow can be continued with the first and second images B1, B2 of the stereo image exposure UEB.

Figure 4:
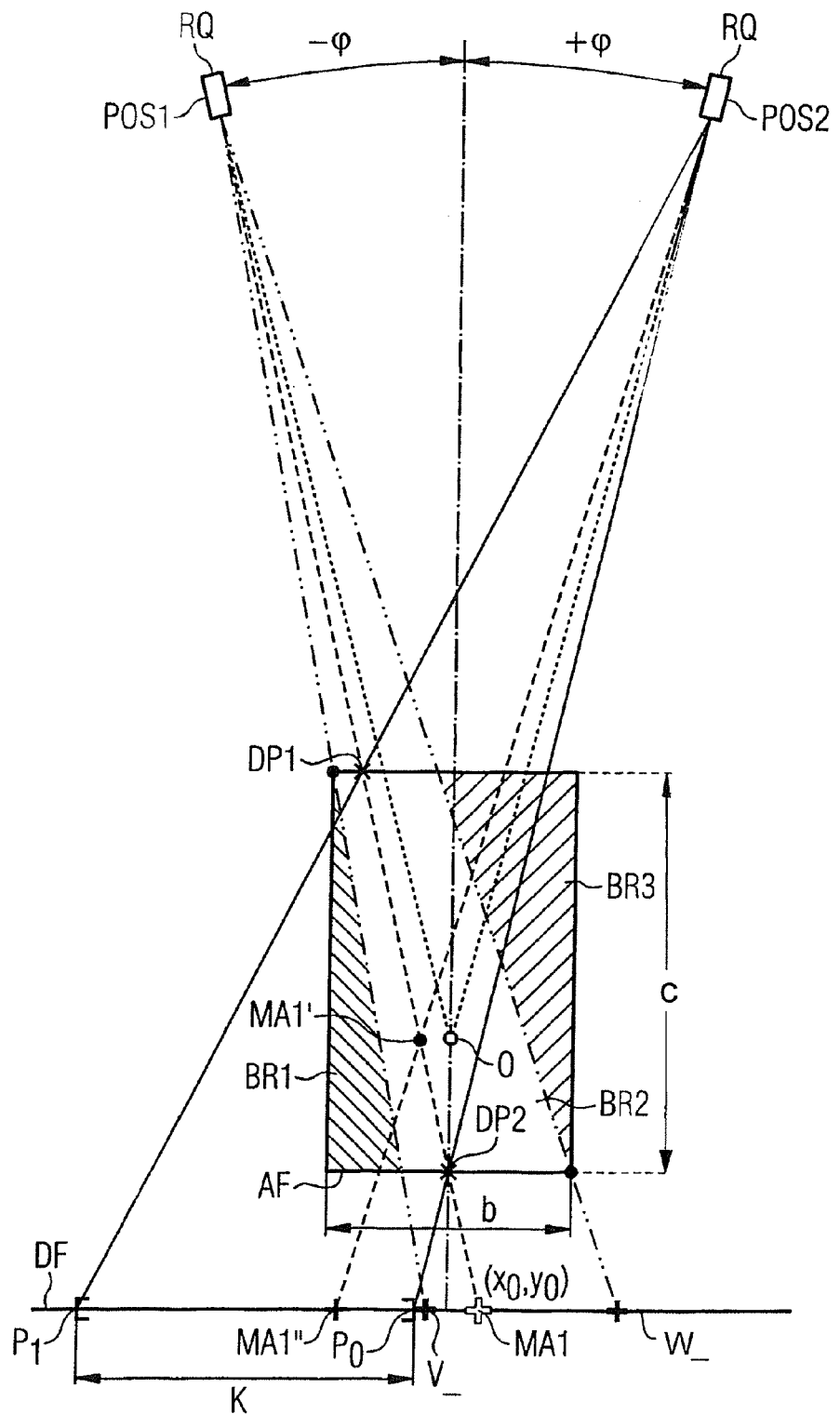
FIG. 4 schematically illustrates a further feature of the device and method according to the invention.

A continuing limitation of a possible association region with regard to a focused first tissue variation MA1, starting from the first image B1 of the stereo image exposure UEB, is shown in FIG. 4. To simplify the connections, only a side view is considered. The first tissue variation in the first and second image is the same tissue variation within the volume that can be biopsied.

Starting from a first marking MA1 (X0, Y0) in the first image B1, a search corridor in the second image B2 is determined with the fourth module SK and visualized by means of the sixth module SPF.

To create the first x-ray image exposure B1, the x-ray generator RQ is moved into a first position POS1. Starting from the first position of the x-ray head RQ, the first tissue variation MA1 is considered in detail at the detector plane DF. A first penetration point DP1 and a second penetration point DP2 on the cuboid of the biopsy-capable volume MP are defined based on the determinable coordinates X0, Y0.

With the coordinates of the penetration points it can be determined whether the tissue variation lies within a first, second or third volume region BR1, BR2, BR3. In the selected exemplary embodiment, the tissue variation lies in the second region BR2. The tissue variation lies within the marking end points v and w plotted on the detector surface. Due to the position X0, Y0 of the first tissue variation MA1 on the detector plane DF, this position can be projected onto the bearing surface AF and the cover surface PP. The penetration points DP1, DP2 that are thereby obtained yield the boundary projection coordinates for x-rays of an x-ray source RQ fixed in a second position POS2. At the same time, the projection of the penetration points onto the detector plane also yields the length of a possible search corridor K in the second image B2 given connection of these projection points P0, P1.

The search corridor K can be additionally limited due to the known travel path of the x-ray head RQ and the projection of the localized tissue variation MA1' on the detector plane DF. For the calculation of the corners P1, P0 on the detector plane DF, the arrangement according to FIG. 4 is based on the same coordinate system as the arrangement according to FIG. 2.

The isocenter O lies in the biopsy-capable volume.

The variable below are defined as follows: l is the distance of the x-ray head RQ from the detector surface DF; t is the distance from detector surface DF to bearing surface AF; h is the distance between bearing surface DF and isocenter O; and an edge length of the volume M is designated with the width b.

In the first x-ray image B1 the x-ray head RQ is moved by the angle $-\Phi$ from the rest position, and in the second x-ray image it is moved by the angle $+\Phi$ from the rest position. If the coordinates X0, Y0 lie within the boundary markers v, q, the corners P0, P1 are calculated according to the following equation: assuming the position of the markings MA1, ..., MAn between the corners $v_+$, $w_+$ in the image B1 on the detector plane DF, the coordinates of the marked regions in the second image MA1, ..., MAn can be determined as follows:

$$v_+ = \frac{bh + t + 1 - h\varphi + t1 - h\varphi}{\cdot p \cdot h + 1 - h\varphi} + r$$

and $$w_+ = \frac{-bh + t + 1 - h\varphi + c + t1 - h\varphi}{\cdot p \cdot h - c + 1 - h\varphi} + r$$

$$x > v_+ \qquad 1$$

$$P = \begin{pmatrix} x - \frac{t+c}{p} \cdot \frac{1 - h\varphi}{h - c + 1 - h\varphi} \\ y \end{pmatrix}.$$

$$P = \begin{pmatrix} \frac{b - 1 - h\varphi}{b + 1 - h\varphi} \cdot x + \cdot r + \frac{b}{p} \cdot \frac{\cdot 1 - h\varphi}{b + 1 - h\varphi} \\ y \end{pmatrix}$$

$$v_+ \geq x \geq w_+: \qquad 2$$

$$P = \begin{pmatrix} x - \frac{t}{p} \cdot \frac{1 - h\varphi}{h + 1 - h\varphi} \\ y \end{pmatrix}$$

$$P = \begin{pmatrix} x - \frac{t+c}{p} \cdot \frac{1 - h\varphi}{h - c + 1 - h\varphi} \\ y \end{pmatrix}.$$

$$x < w_+ \qquad 3$$

$$P = \begin{pmatrix} x - \dfrac{t}{p} \cdot \dfrac{1 - h\varphi}{h + 1 - h\varphi} \\ \\ y \end{pmatrix}$$

$$P = \begin{pmatrix} \dfrac{b + 1 - h\varphi}{b - 1 - h\varphi} \cdot x + \cdot r + \dfrac{b}{p} \cdot \dfrac{\cdot 1 - h\varphi}{b - 1 - h\varphi} \\ \\ y \end{pmatrix}.$$

The specification of the corners follows with exchange of the projections POS1, POS2.

$$v_- = \dfrac{bh + t + 1 - h\ \varphi - c + t1 - h\varphi}{\cdot p \cdot h - c + 1 - h\varphi} + r$$

and $$w_- = \dfrac{-bh + t + 1 - h\varphi - \ t1 - h\varphi}{\cdot p \cdot h + 1 - h\varphi} + r$$

$$x > v_- \qquad 4$$

$$P = \begin{pmatrix} x + \dfrac{t}{p} \cdot \dfrac{1 - h\varphi}{h - c + 1 - h\varphi} \\ \\ y \end{pmatrix}$$

$$P = \begin{pmatrix} \dfrac{b + 1 - h\varphi}{b - 1 - h\varphi} \cdot x + \cdot r + \dfrac{b}{p} \cdot \dfrac{\cdot 1 - h\varphi}{b - 1 - h\varphi} \\ \\ y \end{pmatrix}.$$

$$v_- \geq x \geq w_- \qquad 5$$

$$P = \begin{pmatrix} x + \dfrac{t}{p} \cdot \dfrac{1 - h\varphi}{h + 1 - h\varphi} \\ \\ y \end{pmatrix}$$

$$P = \begin{pmatrix} x + \dfrac{t + c}{p} \cdot \dfrac{1 - h\varphi}{h - c + 1 - h\varphi} \\ \\ y \end{pmatrix}.$$

$$x < w_- \qquad 6$$

$$P = \begin{pmatrix} x + \dfrac{t + c}{p} \cdot \dfrac{1 - h\varphi}{h - c + 1 - h\varphi} \\ \\ y \end{pmatrix}$$

$$P = \begin{pmatrix} \dfrac{b + 1 - h\varphi}{b - 1 - h\varphi} \cdot x \cdot r + \dfrac{b}{p} \cdot \dfrac{\cdot 1 - h\varphi}{b - 1 - h\varphi} \\ \\ y \end{pmatrix}.$$

The y-values in the detector plane result as examples for the case 1 from the following formulas:

$$y = y + \dfrac{\cdot t \cdot 1 - h \cdot \varphi}{h + 1 - h \cdot \varphi}$$

$$y = \dfrac{b - 1 - h\varphi}{b + 1 - h\varphi} \cdot y - \dfrac{\cdot b \cdot 1 - h \cdot \varphi}{b + \cdot 1 - h \cdot \varphi}$$

Figure 5:
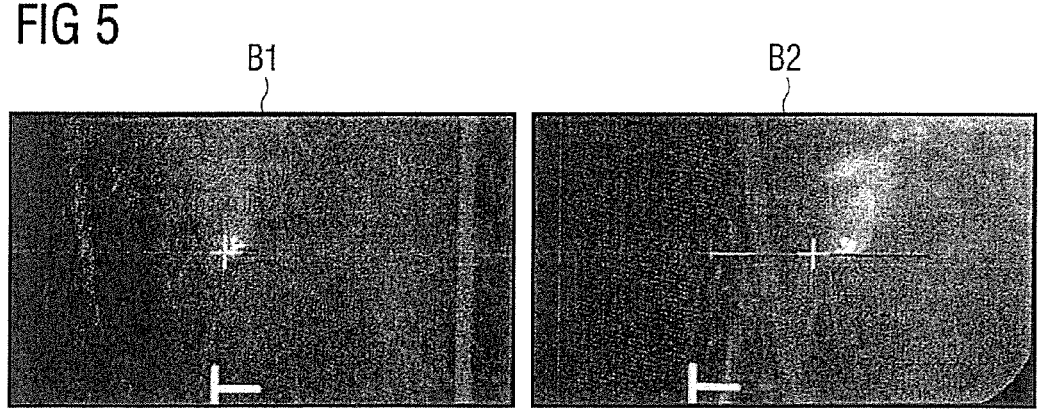
FIG. 5 illustrates a search corridor used in accordance with the invention.

A visualization type for the described search corridor K is reproduced in FIG. 5. In the left image B1, a tissue variation MA1 is localized. This tissue variation MA1 from image 1 lies within the previously described frame RRA and in the search corridor K (as described above) in the second image B2. The tissue variation marked in the first image B1 lies in this emphasized search corridor. Due to the multiple tissue structures and the overlay of the tissue structures based on the 2D exposure in the x-ray images, the device and method according to the invention allow a physician to associate identical tissue structures in the first and second images B1, B2 of the stereo exposure with one another.

Although modifications and changes may be suggested by those skilled in the art, it is the intention of the inventor to embody within the patent warranted hereon all changes and modifications as reasonably and properly come within the scope of his contribution to the art.

We claim as our invention:

1. A device for localization of a tissue variation in an examination subject for a biopsy, comprising:
    an x-ray imaging system;
    a control unit configured to operate the x-ray system to obtain an overview image of an examination subject in whom tissue variations exist, while the examination subject is located in a position in said imaging system;
    said imaging system comprising a display and being configured to display the overview image at said display, as a displayed image, with said tissue variations being visually perceptible in said displayed image;
    said control unit being configured to operate said x-ray imaging system to also obtain a first image of the examination subject in said position and a second image of the examination subject in said position;
    a computer configured to combine said first and second images to form a stereo image of the subject, said first and second images having respective overlapping regions in said stereo image; and
    said computer being configured to automatically determine dimensions of an x-ray field that is generated by said x-ray system that penetrates the examination subject and, from said dimensions, to determine a volume of the examination subject in which a biopsy can be implemented, with said subject in said position in said x-ray system, using said stereo image to show a tissue variation to be biopsied in said biopsy, among said tissue variations in said subject, and to superimpose a visually perceptible frame on said overview image in said displayed image at said display that represents dimensions of said x-ray field limited to said overlapping regions, in order to allow an immediate determination by a viewer of the displayed image as to whether said tissue variation to be biopsied is within said frame and thus can be biopsied while said patent remains in said position in said x-ray imaging system.

2. A device as claimed in claim 1 comprising a search module that specifies a search corridor for identifying identical tissue variations in the subject in the first and second images, and that causes said search corridor to be displayed at said display.

3. A device as claimed in claim 2 wherein said search module limits said search corridor in the second image.

4. A device as claimed in claim 1 wherein said computer is configured to execute a tissue variation recognition algorithm to identify said tissue variations at said display.

5. A method for localization of a tissue variation in an examination subject for a biopsy, using an x-ray imaging system comprising a control unit, a display and a computer, said method comprising:

from said control unit, operating the x-ray system to obtain an overview image of an examination subject in whom tissue variations exist, while the examination subject is located in a position in said imaging system;

at said display, displaying the overview image, as a displayed image, with said tissue variations being visually perceptible in said displayed image;

from said control unit, operating said x-ray imaging system to also obtain a first image of the examination subject in said position and a second image of the examination subject in said position;

in said computer, combining said first and second images to form a stereo image of the subject, said first and second images having respective overlapping regions in said stereo image; and in said computer, automatically determining dimensions of an x-ray field that is generated by said x-ray system that penetrates the examination subject and, from said dimensions, determining a volume of the examination subject in which a biopsy can be implemented, with said subject in said position in said x-ray system, using said stereo image to show a tissue variation to be biopsied in said biopsy, among said tissue variations in said subject, and superimposing a visually perceptible frame on said overview image in said displayed image at said display that represents dimensions of said x-ray field limited to said overlapping regions, in order to allow an immediate determination by a viewer of the displayed image as to whether said tissue variation to be biopsied is within said frame and thus can be biopsied while said patent remains in said position in said x-ray imaging system.

6. A method as claimed in claim 5 comprising, in a search module, specifying a search corridor for identifying identical tissue variations in the subject in the first and second images, and that causes said search corridor to be displayed at said display.

7. A method as claimed in claim 6 comprising, in said search module, limiting said search corridor in the second image.

8. A method as claimed in claim 5 comprising, in executing a tissue variation recognition algorithm to identify said tissue variations at said display.

* * * * *